United States Patent [19]

Kukes

[11] Patent Number: 4,487,986
[45] Date of Patent: Dec. 11, 1984

[54] OLEFIN DISPROPORTIONATION AND CATALYST THEREFORE

[75] Inventor: Semyon Kukes, Bartlesville, Okla.

[73] Assignee: Phillips Petroleum Company, Bartlesville, Okla.

[21] Appl. No.: 195,699

[22] Filed: Oct. 9, 1980

[51] Int. Cl.³ .............................................. C07C 6/00
[52] U.S. Cl. .................................. 585/645; 502/132; 585/646
[58] Field of Search ........................ 585/645, 646, 644

[56] References Cited

U.S. PATENT DOCUMENTS

| | | | |
|---|---|---|---|
| 3,340,322 | 9/1967 | Heckelsberg | 585/643 |
| 3,346,661 | 10/1967 | Wilson et al. | 585/646 |
| 3,418,390 | 12/1968 | Heckelsberg | 585/646 |
| 3,546,311 | 12/1970 | Heckelsberg | 585/645 |
| 3,579,602 | 5/1971 | Rensser | 585/644 X |
| 3,637,893 | 1/1972 | Shingleton | 585/645 X |

OTHER PUBLICATIONS

Bacon et al., "Chemical Abstracts", vol. 41, p. 2937c, (1947).

*Primary Examiner*—Robert V. Hines

[57] ABSTRACT

An improved olefin disproportionation catalyst produced by contacting (a) molybdenum or tungsten oxide supported on inorganic refractory oxide, and (b) a metal dithionite.

7 Claims, No Drawings

OLEFIN DISPROPORTIONATION AND CATALYST THEREFORE

BACKGROUND OF INVENTION

This invention relates to the disproportionation of olefins. In another aspect this invention relates to a disproportionation catalyst. In still another aspect, this invention relates to a novel method for producing a disproportionation reaction.

The disproportionation, or methathesis, of olefins is a reaction in which one or more olefinic compounds are transformed into other olefins of different molecular weights. The disproportionation of an olefin to produce one olefin of a higher molecular weight and one olefin of a lower molecular weight can also be referred to as self-disproportionation. For example, propane can be disproportionated to ethylene and cis- and trans-2-butene. Another type of disproportionation involves the codisproportionation of two different olefins to form still other olefins. An example would be the reaction of one molecule of 2-butene with one molecule of 3-hexene to produce two molecules of 2-pentene.

The term "disproportionation reaction" as used herein is intended to include all variations of disproportionation reactions including:

(1) The disproportionation of an acyclic mono- or polyene having at least three carbon atoms into other mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acrylic mono- or polyene having three or more carbon atoms and a different acyclic mono- or polyene having three or more carbon atoms to produce different acyclic olefins; for example, the conversion of propylene and isobutylene yields ethylene and isopentene;

(3) The conversion of ethylene and an internal acyclic mono- or polyene having four or more carbon atoms to produce other olefins having a lower number of carbon atoms than that of the acyclic mono- or polyenes; for example, the conversion of ethylene plus 4-methylpentene-2 yields 3-methylbutene-1 and propylene;

(4) The conversion of ethylene or an acyclic mono- or polyene having three or more carbon atoms with a cyclic mono- or cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9-decatriene;

(5) The conversion of one or more cyclic mono- or cyclic polyenes to produce a cyclic polyene having a higher number of carbon atoms than any of the starting materials; for example, the conversion of cyclopentene yields 1,6-cyclodecadiene;

(6) The conversion of an acyclic polyene having at least 7 carbon atoms and having at least 5 carbon atoms between any two double bonds to produce acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

Among the catalysts that have been developed for disproportionation are those comprising inorganic refractory oxides containing a catalytic amount of at least one of molybdenum oxide and tungsten oxide. The present invention is based upon the discovery of a way to improve the characteristics of such a catalyst.

SUMMARY OF INVENTION

In accordance with the present invention, a disproportionation catalyst comprising inorganic refractory oxide containing a catalytic amount of at least one of molybdenum oxide and tungsten oxide is improved by admixing therewith a promoting amount of a dithionite salt of a metal of Groups IA and IIB of the Periodic Table of the Elements.

DESCRIPTION OF PREFERRED EMBODIMENTS

The inorganic refractory oxide comprises solid inorganic oxide support containing a major proportion of alumina or silica. Such materials are commonly known as refractory oxides and include, for example, silica, alumina, magnesia-alumina, silica-alumina, titania-alumina, zirconia-alumina, and alumina-titania-zirconia. Preferred refractory metal oxides are alumina refractory oxides, i.e., refractory oxides containing a substantial proportion of alumina, e.g., at least 10 percent by weight of alumina, preferably at least 25 percent of alumina, although still larger proportions of alumina can be used. Generally, the refractory oxide has a surface area of at least 10 $m^2/g$ and preferably the surface area is from about 25 $m^2/g$ to 800 $m^2/g$.

Molybdenum oxide and tungsten oxide can be combined with the refractory oxide support in any conventional manner such as dry mixing, impregnation from a diluent, ion-exchange or the like. The oxides can be added directly or in the form of molybdenum or tungsten that can be converted to oxides by calcination.

The molybdenum or tungsten oxide-alumina composition employed as a catalyst precursor is optionally, and preferably, subjected to pretreatment prior to utilization in preparation of the catalyst. The precise method of pretreatment will depend in part upon the form of chemical combination in which the molybdenum or tungsten components are provided, but in general the pretreatment comprises heating an initially prepared molybdenum or tungsten containing alumina refractory oxide in an atmosphere of a non-reducing gas such as nitrogen, argon, carbon monoxide or oxygen-containing gas, e.g., air. One function served by this type of pretreatment is to convert the molybdenum or tungsten components into the form of the oxide if these components are not initially provided in these forces. For example, initial catalyst components such as ammonium tungstate or ammonium molybdate are converted to the corresponding oxide by heating in a non-reducing atmosphere. The pretreatment temperature is not critical and temperatures from about 350° C. to 800° C. are satisfactory.

The oxide of molybdenum or tungsten is preferably combined with the inorganic oxide solid support in a high positive oxidation state, e.g., hexavalent molybdenum or hexavalent tungsten. The proportion of the molybdenum or tungsten oxide combined with the alumina-containing inorganic oxide can be varied, but generally the inorganic oxide solid contains at least 0.1 percent by weight of the oxide of molybdenum or tungsten with amounts from about 0.2 percent to about 50 percent by weight being preferred, although still larger (major) proportions of molybdenum or tungsten oxide can be used.

The metal dithionite salt can be combined with the thus prepared catalyst in any suitable manner. Preferably, the catalyst is impregnated with a liquid diluent containing the salt. A water solution of the salt is currently preferred. After impregnation the catalyst is then heated in an inert atmosphere, such as nitrogen or argon, to remove the liquid diluent. The temperature employed in removing the diluent can vary widely; however, temperatures in the range of about 400° C. to about 800° C. are currently preferred.

The benefits provided by the dithionite treatment are adversely affected if the catalyst is later exposed to an oxidative atmosphere, especially at elevated temperatures. Accordingly, preferably the catalyst is maintained under a substantially inert atmosphere after the dithionite treatment.

Examples of dithionite salts of Groups IA and IIB include sodium dithionite and zinc dithionite. The optimum amounts of dithionite salt can readily be determined by routine experimentation. Generally, the dithionite salt should be used in an amount in the range of about 0.1 to about 20 weight percent, preferably about 5 to about 15 weight percent, based on the weight of the metal oxide support combination prior to the addition of the dithionite.

The promoted catalyst can be used in disproportionation reactions in a conventional manner. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

The pressure during the disproportionation reaction may vary between wide limits. Pressures between 0.1 and 500 atm. are suitable; preferred pressures are between 0.5 and 250 atm. If possible, the process should be operated at a pressure which is atmospheric or nearly atmospheric so that no vacuum or pressure apparatus is required.

If the reaction is carried out in the liquid phase, solvents or diluents for the reactants may be used. Aliphatic saturated hydrocarbons (e.g. pentane, hexane, cyclohexane, dodecane) and aromatic hydrocarbons such as benzene and toluene are suitable. If the reaction is carried out in the gaseous phase, diluents such as aliphatic hydrocarbons (e.g. methane, ethane) and/or inert gases (e.g., nitrogen, carbon dioxide) may be present. Preferably the disproportionation reaction is effected in the substantial absence of reactive material such as water and oxygen.

The length of time during which the olefinically unsaturated compounds to be disproportionated are contacted with the catalyst is not very critical, and may conveniently vary between 5 seconds and 24 hours, although longer and shorter contact times may be used. The contact time needed to obtain a reasonable yield of disproportionated products depends on several factors such as the activity of the catalyst, temperature, pressure and structure of the olefinically unsaturated compounds to be disproportionated.

The process of the invention is effected batchwise or continuously, with fixed catalyst beds, slurried catalysts, fluidized beds or by using any other conventional contacting technique. The solid disproportionation catalysts are applied in any appropriate form, for example, as powders, flakes, pellets, spheres or extrudates.

The Products. According to the process of the invention two olefinic reactants are disproportionated to a product comprising olefin(s) having a total number of carbon atoms equal to the sum of the carbon atoms of the two olefinic reactants and having a number of ethylenic linkages equal to the sum of the ethylenic double bonds of the reactants.

One variation of the process comprises the disproportionation of two molecules of the same olefinic reactant. The reaction of two molecules of an acyclic olefin of Formula I generally produces one olefin of a higher carbon number and one olefin of a lower carbon number as depicted in equation (1)

$$2RCH=CHR' \rightarrow RCH=CHR + R'CH=CHR' \tag{1}$$

wherein R and R' have the previously stated significance. If R and R' represent identical groups, it is appreciated that the disproportionation reaction will not cause any skeletal changes as the products RCH=CHR and R'CH=CHR' will be equivalent to R'CH=CHR. By way of specific illustration, the reaction of two molecules of propylene produces ethylene and 2-butene. However, the reaction of two molecules of 2-butene produces two molecules of 2-butene. The reaction of two molecules of cyclic olefinic reactant of Formula II, however, produces a single cyclic olefin produced as depicted in equation (2)

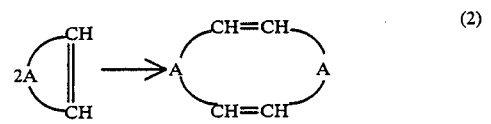

(2)

By way of specific illustration, the reaction of two molecules of cyclooctene produces 1,9-cyclohexadecadiene.

Another variation of the process comprises the disproportionation of two different acyclic olefinic reactants. By way of specific illustration, the reaction of 2-butene and 3-hexene produces two molecules of 2-pentene and the reaction of 2-butene with 1,4-polybutadiene produces two molecules of 1,4-polybutadiene having a molecular weight which is less than the molecular weight of the starting 1,4-polybutadiene.

Still another variation of the process is "ring-opening" disproportionation wherein an acyclic olefinic reactant represented by Formula I is contacted with a cyclic olefinic reactant represented by Formula II. The product of "ring-opening" is a single olefinic compound with one less carbocyclic ring than the cyclic olefinic reactant of Formula II. In terms of the Formulas I and II, the product is represented by Formula III.

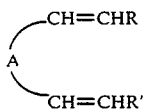

wherein R, R' and A have previously stated significance. By way of specific illustration, from reaction of 2-butene and cyclopentene is produced 2,7-nonadiene. Other typical products include 2,8-decadiene produced by reaction of cyclohexene and 2-butene, 3,8-undecadiene produced from 3-hexene and cyclopentene, 1,5,9-decatriene produced by reaction of ethylene and 1,5-cyclooctadiene, and 1,4-divinylcyclohexane from ethylene and bicyclo(2.2.2)oct-2-ene.

In "ring-opening" disproportionation, the cyclic olefinic reactant is preferably by a monocyclic or a bicyclic olefinic reactant of up to two ethylenic linkages and most preferably is a monocyclic, monoolefinic reactant of from five to eight carbon atoms, and the acyclic olefinic reactant is preferably an internal olefin which is symmetrical about the double bond, i.e., those olefins wherein both R and R' groups are alkyl and R=R'. The molar ratio of cyclic olefinic reactant to the acyclic olefin in ring-opening disproportionation is not critical, although it is frequently useful to employ a molar excess of the acyclic olefin. Molar ratios of acyclic olefin to cyclic olefin reactant from about 1:1 to about 70:1 are satisfactory with molar ratios from about 1:1 to about 0:1 being preferred.

It is appreciated that an olefinic product produced by any variation of the disproportionation process can undergo further disproportionation with another olefin present in the reaction mixture. For example, 1,6-heptadiene produced from reaction of cyclopentene and ethylene can react with another molecule of cyclopentene to produce 1,6,11-dodecatriene, and 1,9-cyclohexadecadiene produced from reaction of two molecules of cyclooctene to give a high molecular weight monocyclic polyene.

The olefinic products, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

EXAMPLE I

One gram of a $WO_3 \cdot SiO_2$ composition containing 6 weight percent $WO_3$ was placed in a tubular quartz reactor of the type generally used for disproportionation reactions. A 5 cc water solution of 0.1 gram $Na_2S_2O_4$ was poured over the catalyst. This was followed by a 5 cc water wash. The resulting catalyst composition was then dried under $N_2$ for 1.5 hours at 550° C.

The dried catalyst was then tested for catalytic activity using purified propylene as a reactant. The reaction was conducted at 455° C. and a gas hourly space velocity of 6000. Conversion was 12.5 percent after 5 minutes and 25.2 percent after 60 minutes.

For comparison, propylene was disproportionated under the same conditions using a $WO_3 \cdot SiO_2$ composition containing 6 weight percent $WO_3$ with no dithionite treatment. With that catalyst the conversion after 5 minutes was only 2.6 percent and after 60 minutes only 11.6 percent.

This establishes that the dithionite treatment provides a significant improvement in catalyst activity.

What is claimed is:

1. A process for the disproportionation of olefins comprising contacting at least two non-conjugated olefinic reactants under suitable reaction conditions with a catalytic amount of a catalyst composition produced by admixing an inorganic refractory oxide containing a catalytic amount of at least one metal oxide selected from molybdenum oxide or tungsten oxide with a promoting amount of a dithionite salt of the formula $Me_xS_2O_4$ wherein Me is a metal selected from Groups IA and IIB of the Periodic Table of the Elements and x is an integer sufficient to satisfy the valence requirements.

2. A process according to claim 1 wherein said inorganic refractory oxide is selected from the group of silica, alumina, and mixtures thereof.

3. A process according to claim 2 wherein said catalytic amount of said metal oxide is in the range of about 1 to about 20 percent of the combined weights of said metal oxide and said refractory oxide prior to the addition of the dithionite salt.

4. A process according to claim 3 wherein the disproportionation is carried out at a temperature in the range of about 20° C. to about 600° C.

5. A process according to claim 4 wherein the dithionite salt is employed in an amount in the range of about 0.1 to about 20 weight percent based on the weight of the metal oxide-refractory oxide combination prior to the addition of the dithionite.

6. A process according to claim 5 wherein said metal oxide is $WO_3$ and said refractory oxide is $SiO_2$.

7. A process according to claim 6 wherein said dithionite is sodium dithionite.

* * * * *